United States Patent [19]

Tiefenbrun et al.

[11] Patent Number: 5,425,757
[45] Date of Patent: Jun. 20, 1995

[54] AORTIC SURGICAL PROCEDURE

[76] Inventors: Jonathan Tiefenbrun, 62 Country Rd., Mamaroneck, N.Y. 10543; Peter J. Wilk, 185 West End Ave., New York, N.Y. 10023

[21] Appl. No.: 65,863

[22] Filed: May 21, 1993

[51] Int. Cl.6 .......................... A61F 2/24; A61B 19/00
[52] U.S. Cl. ............................................ 623/2; 623/1; 623/66; 606/194
[58] Field of Search ............................ 623/66, 1, 11, 2; 128/898; 606/194

[56] References Cited

U.S. PATENT DOCUMENTS

| | | | |
|---|---|---|---|
| 3,626,947 | 12/1971 | Sparks | 623/1 X |
| 3,958,557 | 5/1976 | Sharp et al. | 623/1 X |
| 4,173,981 | 11/1979 | Mortensen | 604/282 |
| 5,042,161 | 8/1991 | Hodge | 128/774 X |
| 5,217,910 | 8/1980 | Khalil | 128/670 |

OTHER PUBLICATIONS

Borst "Occlusion of Intercostal & Lumbar Aortic Branches Using Plastic Plugs" Jul. 1987 p. 91. Ann. Thoracic Surgery.
Sarioglu et al. "A New Surgical Technique for Repair of Aortic Coarctation" 1992 Vascular Surgery pp. 103–108.

*Primary Examiner*—Randall L. Green
*Assistant Examiner*—Rob Clarke
*Attorney, Agent, or Firm*—R. Neil Sudol; Henry D. Coleman

[57] ABSTRACT

In a method in aortic surgery where the aorta of a patient is cut longitudinally to insert a prosthetic vessel or graft to bypass or remove an aneurysm, a plurality of closure elements or plugs are inserted into respective arterial tributaries, and particularly into their openings in the aortic wall, to stop blood backflow from the tributaries, thereby stemming blood loss during the surgery. The closure elements are provided with catch elements such as screw threads or shoulders for prventing inadvertant removal of the plugs from the tributaries. A recess or other element is provided at one end of the closure elements for receiving the operative head of a screwdriver or other tool to facilitate insertion of the closure elements into the branching blood vessels.

6 Claims, 2 Drawing Sheets

5,425,757

AORTIC SURGICAL PROCEDURE

BACKGROUND OF THE INVENTION

This invention relates to a method for use in aortic surgery and more particularly in surgery to treat a patient for an aortic aneurysm. This invention also relates to devices for use in the method.

In a common procedure to treat an aortic aneurysm, the aorta is cut open in the region of the aneurysm and a prosthetic blood vessel or graft is laid in position over the opened portion of the aorta to connect segments thereof located on opposite sides of the aneurysm. Generally, the cutting open of the aorta at the aneurysm reveals a substantial number of openings of small tributaries or branch arteries which lead from the aorta to the spine and back muscles.

Upon the cutting open of the aorta during the aneurysm bypass or replacement procedure, blood flows back through the small tributary arteries and out of the openings or holes in the aortic wall. These openings must be closed at the beginning of the surgical procedure inasmuch as a substantial amount of blood is otherwise lost. Conventional solutions include suturing the openings shut. This technique, however, is time consuming and only moderately successful. Moreover, there is the likelihood that, even under the best of circumstances, the aortic wall will tear under the forces exerted by the sutures and the suturing process.

OBJECTS OF THE INVENTION

An object of the present invention is to provide a method for facilitating the performance of aortic surgery to correct an aneurysm.

Another object of the present invention is to provide such a method which is useful for closing off the small tributary arteries which are connected to the aorta.

Another, more particular, object of the present invention is to provide such a method which is more effective and easier and quicker to use than conventional techniques.

A further particular object of the present invention is to provide such a method which enables injection of a compositon into the arterial system through arterial branches closed by the method of the invention.

Yet another object of the present invention is to provide a device useful in the method of the invention.

These and other objects of the present invention will be apparent from the drawings and detailed descriptions herein.

SUMMARY OF THE INVENTION

A method for use in aortic surgery comprises, in accordance with the present invention, the steps of cutting the aorta of a patient longitudinally, thereby revealing tributary holes, providing a plurality of closure elements, and inserting the closure elements into the holes to stop blood backflow therefrom, thereby stemming blood loss during continued aortic surgery.

According to another feature of the present invention, where at least one of the closure elements is provided along an external surface with a screw thread, the insertion of that closure element includes the step of screwing the closure element into a respective one of the tributary openings or holes.

According to a further feature of the present invention, where at least one of the closure elements is provided with a transversely extending membrane, the method further comprises the steps of providing a hypodermic type needle, puncturing the membrane with the needle and injecting a substance through the needle into the circulatory system of the patient. The substance may be an anticlotting compound, a radiographic composition, a medication, etc.

According to another feature of the present invention, where at least one of the closure elements is hollow and defines a longitudinally extending channel, the method also comprises the steps of providing an insert and inserting the insert into the channel upon insertion of that closure element into a respective tributary hole.

The closure elements may be additionally sutured to the aortic wall.

A closure device for use in aortic surgery comprises, in accordance with the present invention, a body member having a pair of opposite ends, a catch element along the body member between the opposite ends thereof for catching the body member against a vascular wall upon insertion of the body member into a mouth of a blood vessel. An insertion facilitating component is provided on the body member at one of the opposite ends for facilitating insertion of the body member into a mouth of a blood vessel.

The insertion means may merely include a head with a flattened end face or may include a recess for receiving an operative tip of an insertion instrument. For example, where the insertion instrument is a straight edge screw driver, the recess is a slot. Where the insertion instrument has a hexagonal cross-section (e.g., Allen wrench), the recess is hexagonal.

Pursuant to another feature of the present invention, the catch element is a screw thread, preferably made of a resilient (e.g., polymeric) material. Alternatively, the catch element may include at least one annular shoulder on the body of the device.

Pursuant to a supplemental feature of the present invention, the vessel closure device further comprises a self-sealing membrane attached to the body member and extending transversely thereof. The membrane enables the removable insertion of a needle into a closed vessel for purposes of injecting a substance (e.g., an anticlotting agent such as heparin) into the arterial system.

Pursuant to a further feature of the present invention, the vessel closure device further comprises flanges, eyelets or other means on the body member at one of the opposite ends for receiving a suture to enable tying of the body member to an aortic wall.

Where the body member is hollow, a closure element may be inserted into the body member. A membrane may be provided on the plug insert for injection purposes.

A method in accordance with the present invention facilitates the performance of aortic surgery to correct an aneurysm. The method is directed to the closure of the small tributary arteries which are connected to the aorta and is effective, easy and quick to implement, particularly in comparison to conventional techniques.

A device used in performing a method in accordance with the present invention enables injection of a compositon into the arterial system through a closed arterial branch.

DETAILED DESCRIPTION

Figure 1:
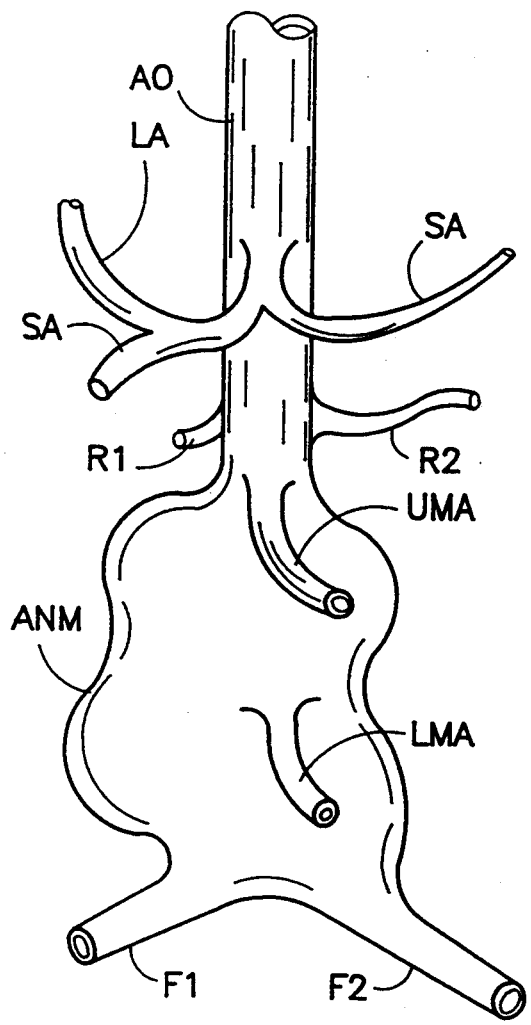
FIG. 1 is a schematic perspective view of a portion of the human arterial system, showing the aorta and major tributary arteries branching therefrom and also showing an aneurysm in the aorta.

As illustrated in FIG. 1, a portion of the human arterial system comprises the aorta AO with major tributary arteries including the splenic artery SA, the renal arteteries R1 and R2, the arteries LA and SA to the liver and stomach, the upper mesenteric artery UMA, the lower mesenteric artery LMA, and the iliac arteries F1 and F2. FIG. 1 also shows an aneurysm ANM in the lower part of the aorta AO above the iliac arteries F1 and F2.

Figure 2:
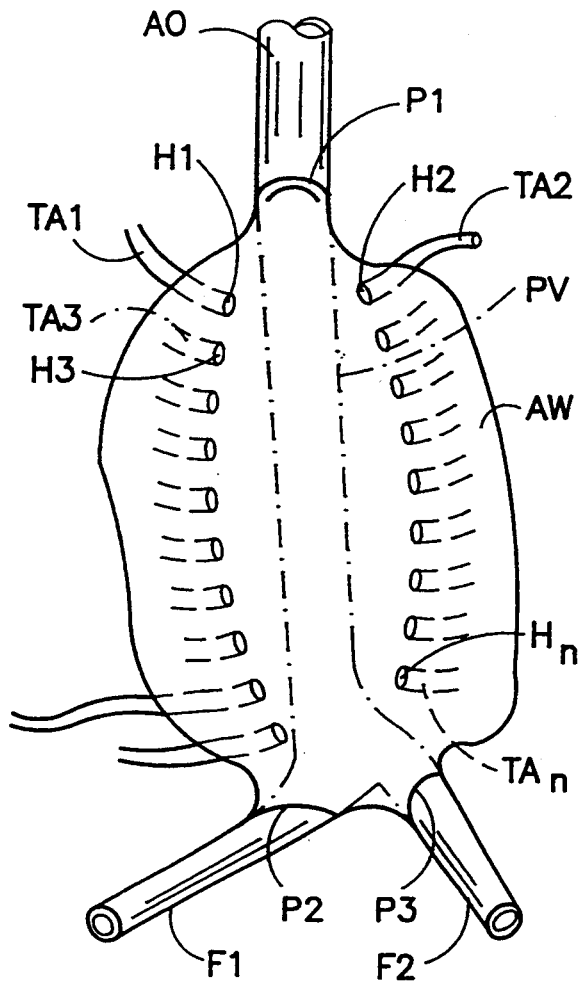
FIG. 2 is a schematic perspective view similar to FIG. 1, showing the aorta laid open at the aneurysm during a stage of corretive surgery performed in accordance with the present invention.

As illustrated in FIG. 2, the aorta AO is severed upstream of aneurysm ANM at point P1 and downstream at points P2 and P3, for purposes of attaching at those points a prosthetic vessel or graft PV. The aortic wall AW is longitudinally cut and laid open, as shown. This procedure reveals a multitude of holes H1, H2, H3, ... Hn which are the openings of small tributary arteries TA1, TA2, TA3, ... TAn extending from the aorta AO to the spinal column and back muscles.

Figure 3:
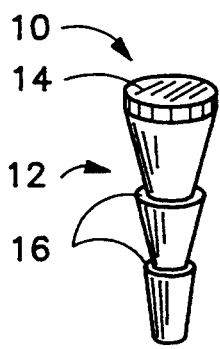
FIG. 3 is a schematic perspective view of a first blood vessel closure device in accordance with the present invention, for use in an aortic bypass procedure in accordance with the present invention.

Holes H1, H2, H3, ... Hn are closed by inserting into each of them the closure device of FIG. 3, 4, 6, 9 or 11 or other plug element equivalent thereto. As shown in FIG. 3, a closure device 10 comprises a generally tapered body member 12 provided at one end with a flat head or face 14 for facilitating the pushing of the device into a tributary artery TA1, TA2, TA3, ... TAn. Body member 12 is further provided along its length with a plurality of longitudinally spaced annular shoulders 16 which serve to anchor the device 10 in a respective tributary artery TA1, TA2, TA3, ... TAn.

Figure 4:
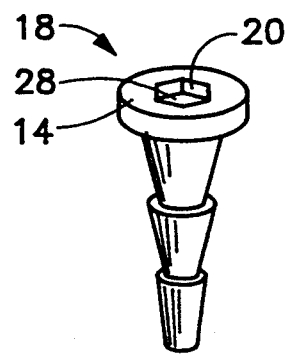
FIG. 4 is a schematic perspective view of a modified blood vessel closure device in accordance with the present invention.
Figure 5:
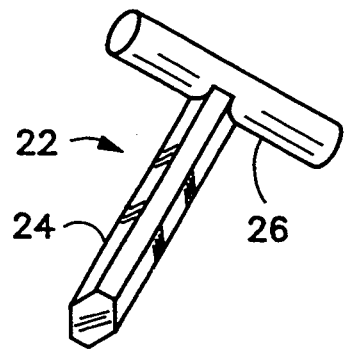
FIG. 5 is a schematic perspective view of a tool for use in inserting the closure device of FIG. 4 into a tributary artery during an aortic bypass procedure in accordance with the present invention.

FIG. 4 illustrates a modified version 18 of the closure device 10 of FIG. 3. Head or face 14 is provided with a hexagonal recess 20 for receiving a distal end of a hexagonal insertion tool 22 shown in FIG. 5. The insertion tool 22 has a hexagonal shaft 24 and a transversely extending handle 26. Closure device 18 may be hollow, with a longitudinally extending channel (not shown). A transversely oriented self-sealing rubber or polyethylene membrane 28 may be provided in the channel for closing the channel while allowing penetration by a hypodermic needle for purposes of injecting a medically indicated composition into the arterial system via device 18 and a respective one of the tributary arteries TA1, TA2, TA3, ... TAn.

Figure 6:
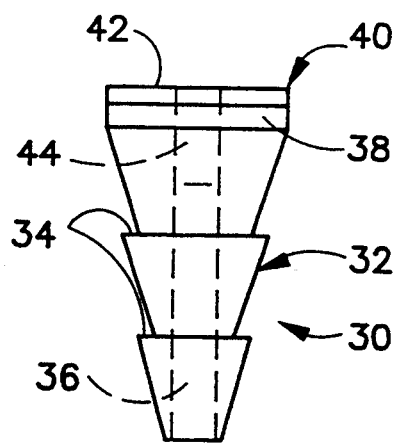
FIG. 6 is a side elevational view of another blood vessel closure device in accordance with the present invention.

As illustrated in FIG. 6, another blood vessel closure device 30 comprises a body member or shaft 32 provided with a plurality of longitudinally spaced annular shoulders 34 which serve to anchor the device 30 in a respective tributary artery TA1, TA2, TA3, ... TAn. Body member or shaft 32 is formed with a longitudinally extending channel 36 which traverses a flat head 38 at one end of body member 32 and which is fitted with a plug or cap element 40.

Figure 7:
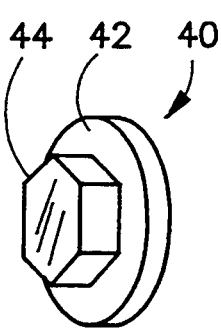
FIG. 7 is a schematic perspective view of a plug or cap element of the closure device of FIG. 6.

As shown in FIG. 7, plug or cap element 40 includes a flattened head 42 and a projection 44 for insertion into channel 36. Projection 44 and channel 36 may be hexagonal, as shown, or some other shape. The hexagonal shape enables device 30 to be inserted or placed via tool 22.

Figure 8:
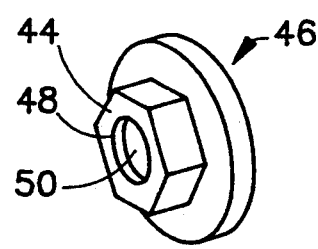
FIG. 8 is a schematic perspective view of a modification of the plug or cap element of FIG. 7.

FIG. 8 depicts a modified plug or cap element 46 wherein projection 44 is axially traversed by a channel 48 which is covered or blocked by a self-sealing membrane 50.

Figure 9:
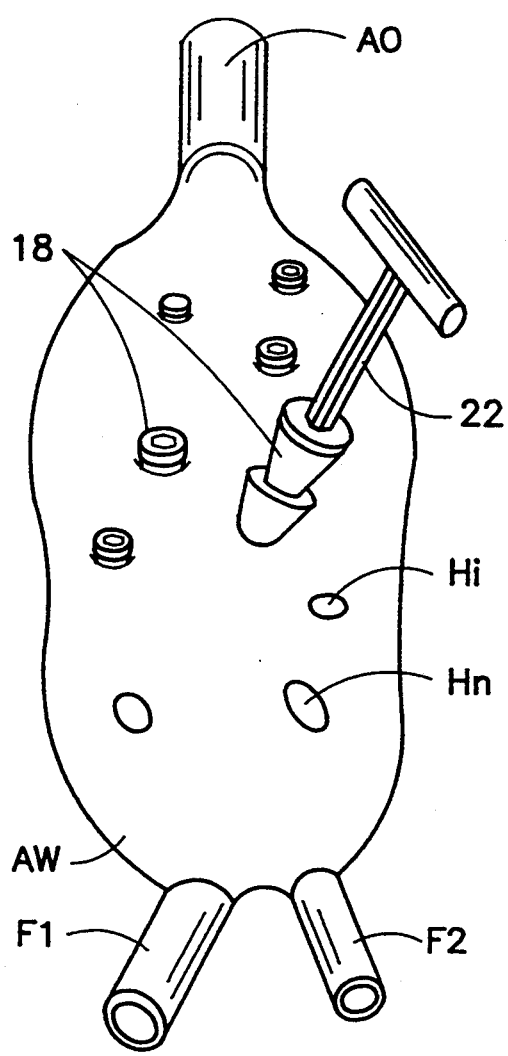
FIG. 9 is a schematic perspective view of a further blood vessel closure device in accordance with the present invention.

FIG. 9 is a schematic perspective view of yet another closure device 52 for use in sealing tributary arteries TA1, TA2, TA3, ... TAn (FIG. 2) by insertion through holes H1, H2, H3, ... Hn. Closure device 52 includes a longitudinally extending body member or shaft 54, a screw thread 56 formed on the outer surface of shaft 54, and a head 58 provided with a recess 60 for receiving a distal end of an insertion tool, e.g., tool 22 of FIG. 5. Screw thread 56 is made of a resilient material such as rubber or polyethylene. Shaft 54 may be hollow and traversed by a self-sealing membrane 62 and/or may be fitted at head 58 with a plug or cap (not shown).

Figure 10:
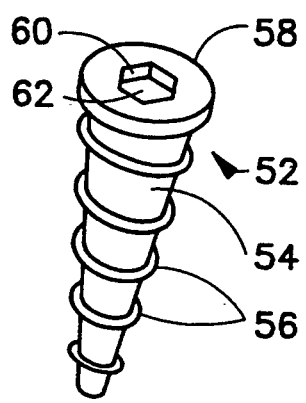
FIG. 10 is a schematic perspective view showing use of the tool of FIG. 5 in inserting the closure device of FIG. 4, 6 or 9.

As depicted in FIG. 10, upon transverse and longitudinal cutting of aorta AO to reveal holes or mouth openings H1, H2, H3, ... Hn or tributary arteries TA1, TA2, TA3, ... TAn, devices 10, 18, 30, 52 are inserted through holes H1, H2, H3, ... Hn to close tributary arteries TA1, TA2, TA3, ... TAn and prevent backflow of blood therefrom. An insertion instrument such as tool 22 of FIG. 5 may be used to place the devices into the holes H1, H2, H3, ... Hn. Where a hollow closure device such as device 30 is used, plugs or caps 40 are inserted into the channels of the closure devices upon insertion thereof into holes H1, H2, H3, ... Hn.

Figure 11:
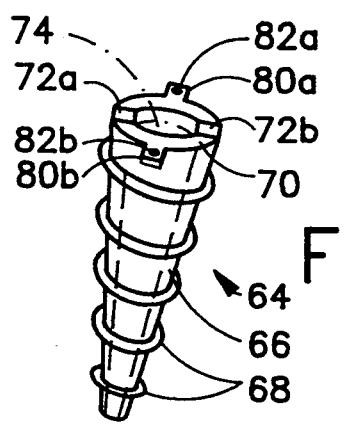
FIG. 11 is a schematic perspective view of yet another blood vessel closure device in accordance with the present invention.
Figure 12:
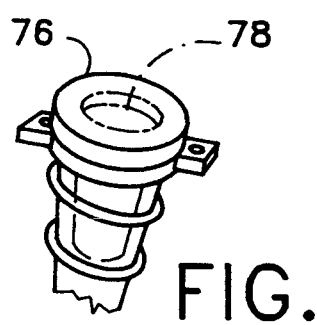
FIG. 12 is a partial schematic perspective view of the closure device of FIG. 11 with a plug or cap inserted, in accordance with the present invention.

As illustrated in FIG. 11, another arterial or venal closure device 64 includes a longitudinally extending body member or shaft 66, a resilient screw thread 68 formed on the outer surface of shaft 66, and a head 70 provided with a pair of slots or recesses 72a and 72b for receiving a straight edge (not shown) of an insertion tool (not shown). Shaft 66 may be hollow and traversed by a self-sealing membrane 74 and/or may be fitted at head 70 with a plug or cap 76 shown in FIG. 12. Plug or cap 76 may be formed with a self-sealing membrane 78.

As further illustrated in FIG. 11, closure device 64 is provided with a pair of diamatrically opposed, radially extending lugs 80a and 80b each formed with a respective eyelet 82a and 82b for receiving a suture thread (not shown).

Upon a screwing of closure device 64 into a hole Hi, H2, H3, ... Hn of a tributary artery TA1, TA2, TA3, ... TAn, a suture may be inserted through eyelets 82a and 82b and the arterial wall AW (FIGS. 2 and 10) to further anchor the closure device in the artery. Subsequently, plug or cap 76 is inserted into the body member or shaft 66 of closure device 64.

A hypodermic type needle (not shown) may be used to puncture membranes 28, 50, 62, 74 and inject a medically indicated substance through the needle into the vascular system of the patient. The substance may be an anticlotting compound, a radiographic composition, a medication, etc.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for use in aortic surgery, comprising the steps of:
   cutting a patient's aorta longitudinally, thereby revealing tributary holes;
   providing a plurality of closure elements, at least one of said closure elements being at least partially hollow and defining a longitudinally extending channel, said one of said closure elements being provided with a membrane extending substantially transversely relative to said channel;
   inserting said closure elements into said holes to stop blood backflow therefrom, thereby stemming blood loss during continued aortic surgery;
   providing a hypodermic type needle;
   upon insertion of said one of said closure elements into a respective one of said holes, puncturing said membrane with said needle; and
   injecting a substance through said needle into a circulatory system of the patient.

2. The method defined in claim 1 wherein at least a selected one of said closure elements is provided along an external surface of said selected one of said closure elements with a screw thread, said step of inserting including the step of screwing said selected one of said closure elements into a respective one of said holes.

3. A method for use in aortic surgery, comprising the steps of:
   cutting a patient's aorta longitudinally, thereby revealing tributary holes;
   providing a plurality of closure elements;
   inserting said closure elements into said holes to stop blood backflow therefrom, thereby stemming blood loss during continued aortic surgery; and
   suturing one end of at least one of said closure elements to a wall of the aorta upon insertion of said one of said closure elements into a respective one of said holes.

4. The method defined in claim 3 wherein at least a selected one of said closure elements is provided along an external surface of said selected one of said closure elements with a screw thread, said step of inserting including the step of screwing said selected one of said closure elements into a respective one of said holes.

5. A method for use in aortic surgery, comprising the steps of:
   cutting a patient's aorta longitudinally, thereby revealing tributary holes;
   providing a plurality of closure elements, at least one of said closure elements being hollow and defining a longitudinally extending channel;
   inserting said closure elements into said holes to stop blood backflow therefrom, thereby stemming blood loss during continued aortic surgery;
   providing an insert; and
   inserting said insert into said channel after insertion of said one of said closure elements into a respective one of said holes.

6. The method defined in claim 5 wherein at least a selected one of said closure elements is provided along an external surface of said selected one of said closure elements with a screw thread, said step of inserting including the step of screwing said selected one of said closure elements into a respective one of said holes.

* * * * *